United States Patent [19]

Nalepa et al.

[11] Patent Number: 5,041,668

[45] Date of Patent: Aug. 20, 1991

[54] SECONDARY DIAMINES

[75] Inventors: Christopher J. Nalepa; J. Kenneth Presswood; Gordon G. Knapp, all of Baton Rouge, La.

[73] Assignee: Ethyl Corporation, Richmond, Va.

[21] Appl. No.: 338,985

[22] Filed: Apr. 14, 1989

[51] Int. Cl.$^5$ ............................................. C07C 211/51
[52] U.S. Cl. ..................................... 564/330; 564/305
[58] Field of Search ........................ 564/330, 331, 305

[56] References Cited

U.S. PATENT DOCUMENTS 3,322,810  5/1967  Olin .................................. 564/330 X
4,083,870  4/1978  Buysch et al. ...................... 564/330

OTHER PUBLICATIONS

Stroh et al., "Chemical Abstracts", vol. 52, pp. 53171–53181 (1958).
Andres et al., "Chemical Abstracts", vol. 63, pp. 1964–1965 (1965).
Klebert, "Chemical Abstracts", vol. 67, p. 8620, Section No. 91337n (1967).
Hiroyoshi, "Chemical Abstracts", vol. 69, p. 9141, Section No. 97366j (1968).

*Primary Examiner*—Richard L. Raymond
*Attorney, Agent, or Firm*—Patricia J. Hogan; Richard J. Hammond

[57] ABSTRACT

Aromatic diamines having one or two benzene rings, two ar-N-methylamino substituents, and ar-alkyl substituents in all positions ortho to the amino substituents are novel compounds which can be used in the preparation of polyurethanes, polyureas, polyurethane-urea polymers, and epoxy resins.

6 Claims, No Drawings

SECONDARY DIAMINES

FIELD OF INVENTION

This invention relates to aromatic diamines and more particularly to sterically hindered secondary aromatic diamines which can be used in the preparation of polyurethane, polyurea, polyurethane-urea, and epoxy resins.

BACKGROUND

There are many polyfunctional compounds, including diols and aromatic diamines, which are known to be useful as chain extenders in the preparation of polyurethane, polyurea, and polyurethane-urea polymers and/or as curing agents for epoxy resins. None of these compounds has a reactivity such as to make it universally ideal, and many fail to provide satisfactory properties in the products made by their use. Thus, there is still a need to find other compounds capable of serving as chain extenders or curing agents.

U.S. Pat. Nos. 4,806,616 (Baumann et al.) teaches the use of certain N,N'-dialkylphenylenediamines as chain extenders in preparing polyurethanes and polyureas by RIM processes.

SUMMARY OF THE INVENTION

An object of this invention is to provide novel sterically hindered secondary aromatic diamines.

Another object is to provide polyurethane, polyurea, polyurethane-urea, and epoxy resins prepared from such aromatic diamines.

These and other objects are attained by (A) providing an aromatic diamine having one or two benzene rings, two ar-N-methylamino substituents, and ar-alkyl substituents in all positions ortho to the amino substituents and (B) when desired, using the aromatic diamine to prepare a polyurethane, polyurea, polyurethane-urea, or epoxy resin.

DETAILED DESCRIPTION

The aromatic diamines of the invention may be any of the aromatic diamines described in the preceding paragraph, including such diamines wherein the alkyl groups have rather long carbon chains, e.g., chains of up to about 20 carbons. However, it is generally preferred that the compounds be aromatic diamines in which the ar-alkyl substituents are straight- or branched-chain alkyl groups of 1-6 carbons, e.g., methyl, ethyl, propyl, isopropyl, butyl, t-butyl, pentyl-hexyl, etc. These alkyl substituents may be the same or different.

In a preferred embodiment of the invention, the aromatic diamine is a compound corresponding to the formula:

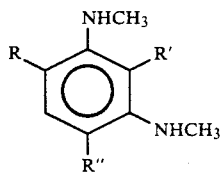

wherein R, R', and R" are independently selected from alkyl groups containing 1-6 carbons; and it is most preferably such a compound in which at least two of the alkyl substituents contain at least two carbons. Of these compounds, those particularly preferred are the N,N'-dimethyl-3,5-diethyl-2,4-diaminotoluene, N,N'-dimethyl-3,5-diethyl-2,6-diaminotoluene, and mixtures thereof.

In another preferred embodiment of the invention, the aromatic diamine is a compound corresponding to the formula:

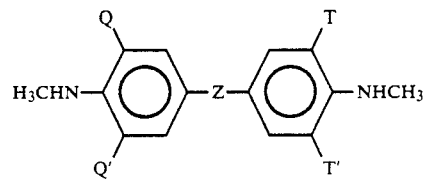

wherein Q, Q', T, and T' are independently selected from alkyl groups containing 1-6 carbons and Z is an alkylidene group containing 1-3 carbons. A particularly preferred aromatic diamine of this type is N,N'-dimethyl-3,3',5,5'-tetraethyl-4,4'-diaminodiphenylmethane.

Regardless of the particular type of compound involved, the secondary aromatic diamines of the invention are prepared by reacting formaldehyde with the primary aromatic diamine corresponding to the desired secondary aromatic diamine (i.e., an aromatic diamine having one or two benzene rings, two primary amino groups attached to the ring or rings, and ar-alkyl substituents in all positions ortho to the amino substituents) and reducing the -N=CH$_2$ groups of the resultant aromatic diimine.

The primary aromatic diamines used as starting materials are well known and include, e.g., 3,5-diethyl-2,4-diaminotoluene, 3,5-diethyl-2,6-diaminotoluene, DETDA (a mixture of 3,5-diethyl-2,4-diaminotoluene and 3,5-diethyl-2,6-diaminotoluene), 1,3,5-triethyl-2,6-diaminobenzene, 3,5-diisopropyl-2,4-diaminotoluene, 3,5-di-sec-butyl-2,6-diaminotoluene, 3-ethyl-5-isopropyl-2,4-diaminotoluene, 3,3',5,5'-tetraethyl-4,4'-diaminodiphenylmethane (MBDEA), 3,3',5,5'-tetraisopropyl-4,4'-diaminodiphenylmethane, 3,3'-dimethyl-5,5',-di- t-butyl-4,4'-diaminodiphenylmethane.

Except for the use of such aromatic diamines, the formaldehyde/amine reaction is conducted by techniques known for converting amines to imines, e.g., the techniques disclosed in March, *Advanced Organic Chemistry*, Second Edition, McGraw-Hill (New York), page 817 (1977), and the references disclosed therein. It is generally preferred to employ 2-4 mols of formaldehyde per mol of aromatic diamine, to incorporate the formaldehyde in the form of paraformaldehyde, and to reflux a mixture of the reactants in toluene or other solvent which azeotropes with water in order to form the diimine, the water of reaction being removed during the course of the reaction.

Actually, it is somewhat surprising both that the diimine intermediates can be prepared by this process and that they are stable and isolable. The literature indicates that formaldehyde is analogous to higher aldehydes and to ketones in the iminization of amines, but it has not been found possible to obtain imines from the aromatic diamines used to prepare the present diimines when attempts have been made to react those diamines with acetaldehyde or acetone in the presence or absence of catalysts. Also, even though March indicates that the presence of an aryl group on the nitrogen or carbon of the imine group makes an imine stable, more recent literature (e.g., Distefano et al., *J. Chem. Soc. Perkin Trans. II*, 1985, pp. 1623-1627) indicates that at least some of the compounds previously believed to be stable aromatic imines had been misidentified and were really polymers formed from unstable imines.

The reduction of the diimine intermediates to the secondary diamines is accomplished by known techniques for reducing imino groups, e.g., the techniques taught by March on page 34. Of these known techniques, reduction with lithium aluminum hydride is preferred.

When the sterically hindered secondary aromatic diamines are to be used as chain extenders in the preparation of polyurethane, polyurea, or polyurethane-urea polymers, they are simply substituted for the chain extenders that have previously been used in such processes or used in conjunction with the known chain extenders, e.g., primary aromatic diamines such as those mentioned above; the aromatic polyamines of U.S. Pat. Nos. 3,428,610 (Klebert), 4,218,543 (Weber et al.), 4,595,742 (Nalepa et al.), and 4,631,298 (Presswood), the teachings of all of which are incorporated herein in toto by reference; polyhydroxyalkanes containing 2–6 carbons and 2–3 hydroxyl groups, such as ethylene glycol, the 1,2- and 1,3-propylene glycols, the 1,4-, 1,2-, and 2,3-butanediols, 1,5-pentanediol, neopentyl glycol, 1,6-hexanediol, glycerol, 1,2,4-butanetriol, 1,2,6-hexanetriol; and mixtures thereof. Thus, the chain extender or mixture of chain extenders is reacted with an organic polyisocyanate and an active hydrogen-containing organic compound or with a prepolymer thereof having a free -NCO content of at least 0.1% by weight to form the desired polymer. Exemplary of the isocyanates and active hydrogen-containing organic compounds that can be used are those taught in Nalepa et al.

When the sterically hindered secondary aromatic diamines are to be used as curing agents for epoxy resins, they are just substituted for the curing agents that have previously been used to cure such resins or used in conjunction with the known curing agents, e.g., the aromatic polyamines and/or polyhydroxyalkanes described above as known chain extenders. The epoxy resin may be any epoxy resin, i.e., it may be saturated or unsaturated, aliphatic, cycloaliphatic, aromatic, or heterocyclic. Exemplary of such resins are those taught in Lee et al., *Handbook of Epoxy Resins*, McGraw-Hill (New York), 1967, the teachings of which are incorporated herein in toto by reference.

The following examples are given to illustrate the invention and are not intended as a limitation thereof.

EXAMPLE I

Part A

Preparation of DETDA Diimine

A suitable reaction vessel was charged with 100.4g (0.564 mol) of DETDA, 54.2g (1.81 mol) of paraformaldehyde, 280 mL of toluene, and 0.2g of sodium hydroxide. The mixture was refluxed with azeotropic removal of water for two hours, at which time no more water was collected. The mixture was then cooled and determined by vpc analysis to contain 90.2 area % DETDA diimine, a mixture of compounds corresponding to the formulas:

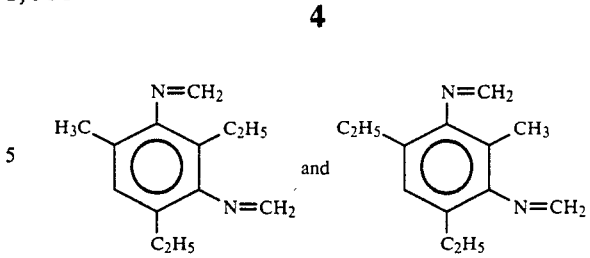

An additional 5.0g of paraformaldehyde was added to the reaction mixture, which was then refluxed for an additional 1.5 hours. Vpc analysis of the resultant solution showed 92.8 area % DETDA diimine, with the remainder being starting material and other impurities.

Part B

Preparation of DM-DETDA

A suitable reaction vessel was charged with 21.7g (0.572 mol) of lithium aluminum hydride and 800 mL of diethyl ether, after which the product solution of Part A was added over a period of one hour. The temperature of the reaction mixture reached a maximum of 42° C. The reaction mixture was stirred for an additional half hour and then worked up by the successive addition of 22 mL of water, 22 mL of 15% aqueous sodium hydroxide, and 66 mL of water. It was then filtered through a Buchner funnel, and the filtrate was distilled under reduced pressure through a 6-inch (15.2-cm) Vigreux column affording 84.8g (74.4% overall yield from DETDA) of a pale yellow liquid having a boiling point of 115°–138° C. at 1.8 mm. Vpc analysis showed the presence of 87.4 area % DM-DETDA, a mixture of N,N'-dimethyl-3,5-diethyl-2,4-diaminotoluene and N,N'-dimethyl-3,5-diethyl-2,6-diaminotoluene. The remainder of the product was essentially N-methyl DETDA.

EXAMPLE II

Part A

Preparation of MBDEA Diimine

A suitable reaction vessel was charged with 105.1g (0.339 mol) of MBDEA, 26.5g (0.883 mol) of paraformaldehyde, 300 mL of toluene, and 0.2g of sodium hydroxide. The mixture was refluxed with azeotropic removal of water for 1.5 hours, then cooled, and determined by vpc analysis to contain 95.4 area % MBDEA diimine, a compound corresponding to the formula:

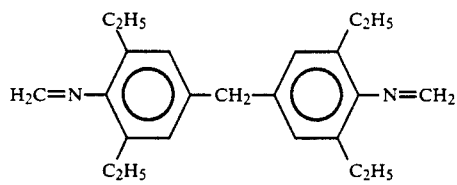

An additional 5.0g of paraformaldehyde was added to the reaction mixture, which was then refluxed for an additional hour. Vpc analysis of the resultant solution indicated 98.2 area % MBDEA diimine, with the remainder being starting material and other impurities. Toluene was removed under reduced pressure, and the material was filtered through glass wool to provide 98.2g (85.1% yield) of MBDEA diimine as a dark oil.

Part B

Preparation of DM-MBDEA

A suitable reaction vessel was charged with 6.8g (0.179 mol) of lithium aluminum hydride and 200 mL of diethyl ether, after which a solution of 60.0g (0.176 mol) of MBDEA diimine in 100 mL of toluene was added to the reaction mixture. An additional 450 mL of diethyl ether was then added to the reaction mixture, which was subsequently stirred and worked up by the successive addition of 7 mL of water, 7 mL of 15% aqueous sodium hydroxide, and 7 mL of water. After filtration through a Buchner funnel and removal of solvent, 54.9g (90.6% yield) of a brown oil was isolated. Vpc analysis indicated 83.5 area % DM-MBDEA, i.e., N,N'-dimethyl-3,3',5,5'-tetraethyl-4,4'-diaminodiphenylmethane. The remainder of the product was N-methyl MBDEA and other impurities.

EXAMPLE III

Reactivity Determinations in a TDI-Based Prepolymer

A series of reaction mixtures was prepared by mixing a preheated stoichiometric portion of a chain extender with 50g of a commercial toluenediisocyanate/polytetramethylene glycol ether prepolymer having a free -NCO content of 6.0% preheated to 80° C. in a polypropylene cup. The reactivity was then determined by measuring the pour time (the expiration of the time after mixing when the reaction mixture could be poured out of the cup), gel time (the expiration of the time after mixing when the reaction mixture could flow under its own weight when the cup was rotated), and firm time (the amount of time after mixing until the reaction mixture would offer substantial resistance to manual pressure). The chain extenders used are indicated in Table I, which also shows the reactivity data in hours (hrs), minutes ('), and seconds ("). In this table, as well as elsewhere in the specification, E-300 represents a mixture of 3,5-di(methylthio)-2,4-diaminotoluene and 3,5-di(methylthio)-2,6-diaminotoluene, U-4200 represents N,N'-di-sec-butyl-4,4'-diaminodiphenylmethane, and the ratios shown are mol ratios.

TABLE I

| Chain Extender | Pour Time | Gel Time | Firm Time |
| --- | --- | --- | --- |
| E-300 | 3'30" | 4'15" | 5'30" |
| U-4200 | 20'00" | 39'00" | >2 hrs |
| DM-DETDA | 125'00" | — | 16 hrs |
| E-300/U-4200 (75/25) | 4'30" | 6'35" | 9'00" |
| E-300/U-4200 (50/50) | 6'15" | 10'30" | 19'00" |
| E-300/U-4200 (25/75) | 11'00" | 16'00" | 70'00" |
| E-300/DM-DETDA (75/25) | 3'15" | 4'10" | 5'15" |
| E-300/DM DETDA (50/50) | 3'30" | 4'35" | 6'15" |
| E-300/DM-DETDA (25/75) | 7'00" | 11'15" | 21'00" |

EXAMPLE IV

Reactivity Determinations in an MDI-Based Prepolymer

A series of reaction mixtures was obtained by repeating Example III except for employing a commercial diphenylmethanediisocyanate/polytetramethylene ether glycol prepolymer having a free -NCO content of 6.2% as the prepolymer and employing the chain extenders indicated in Table II, which also shows the reactivity data.

TABLE II

| Chain Extender | Pour Time | Gel Time | Firm Time |
| --- | --- | --- | --- |
| DETDA | — | 0.1' | 0.5' |
| MBDEA | — | 0.1' | 0.4' |
| DM-DETDA | 8' | 36' | >75' |
| DM-MBDEA | 1' | 7' | 30' |

As demonstrated in the preceding examples, the diamines of the invention have reactivities such as to make them useful alone or in combination with other chain extenders in the preparation of polyurethane, polyurea, and polyurethane-urea polymers. Being slower than the known diamines E-300, U-4200, DETDA, and MBDEA, their use leads to increased working time, while their mixtures with E-300 provide quicker cures than comparable U-4200/E-300 mixtures.

The following example demonstrates that the use of the novel diamines permits the formation of polyurethanes having desirably low compression set and high tensile strength.

EXAMPLE V

Physical Property Determinations in a TDI-Based Prepolymer

A series of polyurethanes was prepared by mixing chain extenders (and, in the preparation of Polyurethane C, 40 phr of a commercial plasticizer) with a commercial toluenediisocyanate/polytetramethylene glycol ether prepolymer having a nominal free -NCO content of 6.01%, degassing the mixtures at 90° C., pouring them into molds, and curing them. When Cure A was used, the composition was heated in the mold for 30 minutes at 100° C. and then post-cured for about 18 hours at 100° C. When Cure B was used, the composition was cured by heating it in the mold for about 18 hours at 100° C. Table III identifies the chain extenders employed, shows the stoichiometry (i.e., the percentage of the stoichiometric amount of chain extender) used, and also shows the physical properties determined by the usual ASTM procedures.

TABLE III

|  | A | B | C | D | E |
| --- | --- | --- | --- | --- | --- |
| Chain Extender |  |  |  |  |  |
| E-300, mol % | 50 | 50 | 100 | — | — |
| DM-DETDA, mol % | 50 | — | — | 100 | — |
| U-4200, mol % | — | 50 | — | — | 100 |
| Stoichiometry, % | 95.2 | 95.1 | 95.6 | 95.0 | 94.6 |
| Cure Conditions | A | A | A | B | B |
| Physical Properties |  |  |  |  |  |
| Hardness, A | 82 | 78 | 83 | 66 | 60 |
| Hardness, D | 29 | 27 | 28 | — | — |
| Tensile Strength, MPa | 31.2 | 30.9 | 19.2 | 23.3 | 18.5 |
| M-100, MPa | 5.3 | 4.6 | 6.1 | 1.8 | 1.7 |
| M-300, MPa | 15.7 | 14.4 | 9.7 | 5.9 | 3.0 |
| Elongation, % | 380 | 380 | 470 | 410 | 470 |
| Die C Tear, kg/m | 3929 | 4!07 | 3929 | 2680 | 2322 |
| D-470 Tear, kg/m | 1250 | 1250 | 1071 | 750 | 411 |
| Compression Set, % | 22 | 50 | 48 | 20 | 77 |
| Resilience, % | 28 | 22 | 46 | 18 | 7 |

The following example shows that the secondary diamines of the invention can be used to prepare epoxy resins having acceptable glass transition temperatures and onset exothermic temperatures high enough to make them particularly useful for preparing prepregs.

EXAMPLE VI

Epoxy Resin Studies

The reactivities of DM-DETDA and DM-MBDEA were evaluated by mixing each of them in substantially equivalent amounts with a commercial diglycidyl ether of bisphenol A having an epoxide equivalent of 183, placing a drop of the sample to be tested in a Tg pan, scanning with a DSC at a heating rate of 10° C./min from 30° C. to 300°–310° C., and determining the onset and peak exothermic temperatures as well as the glass transition temperatures. The results are shown in Table IV.

TABLE IV

| Curing Agent | Tg (°C.) | Onset (°C.) | Peak (°C.) |
| --- | --- | --- | --- |
| DM-DETDA | 82 | 158 | 210 |
| DM-MBDEA | 75 | 162 | 220 |

It is obvious that many variations may be made in the products and processes set forth above without departing from the spirit and scope of this invention.

What is claimed is:

1. An aromatic diamine of the formula

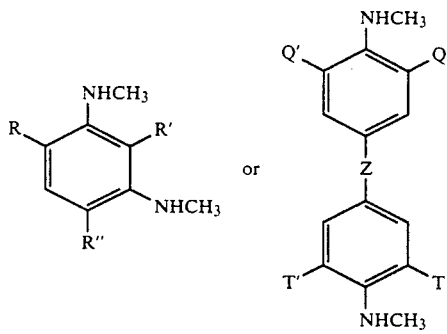

where R, R' and R" are independently selected from alkyl groups containing 1 to 6 carbons; Q, Q', T and T' are independently selected from alkyl groups containing 1–6 carbons; and Z is an alkylidene group containing 1 to 3 carbons.

2. An aromatic diamine of claim 1 wherein at least two of the alkyl substituents contain at least two carbons.

3. An aromatic diamine of claim 2 which is N,N'-dimethyl-3,5-diethyl-2,4-diaminotoluene.

4. An aromatic diamine of claim 2 which is N,N'-dimethyl-3,5-diethyl-2,6-diaminotoluene.

5. An aromatic diamine of claim 1 which is N,N'-dimethyl-3,3'-5,5'-tetraethyl-4,4'-diaminodiphenylmethane.

6. An aromatic diamine which is a mixture of N,N'-dimethyl-3,5-diethyl-2,4-diaminotoluene and N,N'-dimethyl-3,5-diethyl-2,6-diaminotoluene.

* * * * *